United States Patent
Schläpfer et al.

[11] Patent Number: 6,077,262
[45] Date of Patent: Jun. 20, 2000

[54] POSTERIOR SPINAL IMPLANT

[75] Inventors: Johannes F. Schläpfer, Leimen; Martin Hess, Holstein; Rene Schelker; Ralf Hagmann, both of Bennwil, all of Switzerland

[73] Assignee: Synthes (U.S.A.), Paoli, Pa.

[21] Appl. No.: 08/803,550

[22] Filed: Feb. 20, 1997

Related U.S. Application Data

[63] Continuation of application No. 08/405,090, Mar. 16, 1995, abandoned, which is a continuation-in-part of application No. 08/313,031, Sep. 23, 1994, abandoned, and a continuation-in-part of application No. 08/400,482, Mar. 8, 1995, Pat. No. 5,520,689, which is a continuation of application No. 08/070,941, Jun. 4, 1993, abandoned.

[51] Int. Cl.[7] .................................................. A61B 17/56
[52] U.S. Cl. ............................................ 606/61; 606/72
[58] Field of Search ........................... 623/17.11; 606/61, 606/66, 69, 72–73

[56] References Cited

U.S. PATENT DOCUMENTS

| | | | |
|---|---|---|---|
| 4,055,385 | 10/1977 | Bjors | 403/362 |
| 4,653,481 | 3/1987 | Howland et al. | 128/69 |
| 5,067,955 | 11/1991 | Cotrel | 606/61 |
| 5,129,388 | 7/1992 | Vignaud et al. | 606/61 |
| 5,360,431 | 11/1994 | Puno et a. | 623/17 |
| 5,385,583 | 1/1995 | Cotrel | 623/17 |
| 5,443,467 | 8/1995 | Biedermann et al. | 606/61 |
| 5,520,689 | 5/1996 | Schalpfer et al. | 606/61 |
| 5,536,268 | 7/1996 | Griss | 606/61 |
| 5,545,165 | 8/1996 | Biedermann et al. | 606/61 |
| 5,738,685 | 4/1998 | Halm et al. | 606/61 |

FOREIGN PATENT DOCUMENTS

| | | | |
|---|---|---|---|
| 0 441 729 | 8/1991 | European Pat. Off. | |
| 0 465 158 | 1/1992 | European Pat. Off. | |
| 3 800 052 | 7/1989 | Germany . | |
| 0348272 | 12/1989 | Germany | 623/17 |
| 4 110 002 | 5/1992 | Germany . | |

*Primary Examiner*—Bruce Snow
*Attorney, Agent, or Firm*—Fish & Richardson P.C.

[57] ABSTRACT

A spinal screw or hook has a slotted head to receive a support rod. A two-piece rod retainer is provided with an outer ring-like collar locked into the interior of the slotted head and a fastener extending through the collar to contact a support rod in the bottom of the slot.

50 Claims, 7 Drawing Sheets

POSTERIOR SPINAL IMPLANT

This is a continuation of Ser. No. 08/405,090 filed Mar. 16, 1995, now abandoned, which is a continuation-in-part of Ser. No. 08/313,031, filed Sep. 23, 1994, now abandoned; and a continuation-in-part of Ser. No. 08/400,482, filed Mar. 8, 1995, now U.S. Pat. No. 5,520,689, which is a continuation of Ser. No. 08/070,941, filed Jun. 4, 1993, now abandoned.

FIELD OF THE INVENTION

This application is a continuation-in-part of our copending application Ser. No. 08/313,031, filed Sep. 23, 1994.

The present invention is concerned with a posterior spinal implant.

BACKGROUND OF THE INVENTION

Posterior spinal implants serve to correct sagittal spinal deformities (kyphosis, spondylolisthesis) or to act as stabilizers when there is no correction (degenerative instabilities). As a rule they comprise a head having a slot for receiving a support rod, an anchoring segment connected to said head and a tightening screw positioned to press on a support bar in the slot of the head. A stabilizing element may also be present on the head.

The anchoring segment may be a screw or hook. The screw may be fastened directly above the pedicle of the vertebral body. The hook may be suspended from the vertebra. In relation to the number of vertebrae to be corrected or stabilized, several screws or hooks firmly joined to the support rod and thus fixed in place are required for spinal correction or stabilization.

In most known spinal implants, the tightening screw is directly screwed into the head after the support rod has been inserted into the slot. Such practice has a number of drawbacks.

Because the U-shaped slot receives the support rod, the end of the head consists merely of two tulip-shaped jaws. Thus, the tightening screw rests only in the threads of these jaws. When the tightening screw is screwed in under pressure, the surgeon has trouble sensing whether the screw is properly engaging the thread. Furthermore, to prevent the slot from widening, a stabilizing element must be added.

French patent document FR-A 2,624,720 discloses an implant wherein the two legs of the head forming a U-shaped slot have an external thread which may receive a screw-on cap through a central threaded part of which an actual fixation part can be screwed in. However, the manufacture of this known device is difficult. Moreover, it leads to an undesired enlargement of the head with respect to both height and diameter.

SUMMARY OF THE INVENTION

The foregoing disadvantages are relieved by an implant according to the invention which comprises an anchoring segment for attachment to the bone and a head, the head comprising two legs defining a slot for receiving a support rod, a cylindrical closure element in said slot having locking means for engagement with said legs and an aperture, and a fastening element for insertion through said aperture to engage a support rod in said slot.

The aperture in the slot may be threaded offering the substantial advantage that the fastener can be inserted into a closed thread. With an open, slotted thread, high friction arises because of the lack of congruence between the inner and outer threads. This friction may be so high that cold-welding takes place between the fastener and the head.

The invention offers another advantage in that the fastener does not increase the size of the head. Thus, the implant is more compatible.

BRIEF DESCRIPTION OF THE DRAWINGS

The invention will be further described with reference to the accompanying drawings. In the drawings only screws are shown as the anchoring segments, though it will be understood that hooks may also be used.

In the drawings.

DETAILED DESCRIPTION OF THE PREFERRED EMBODIMENTS

Figure 1:
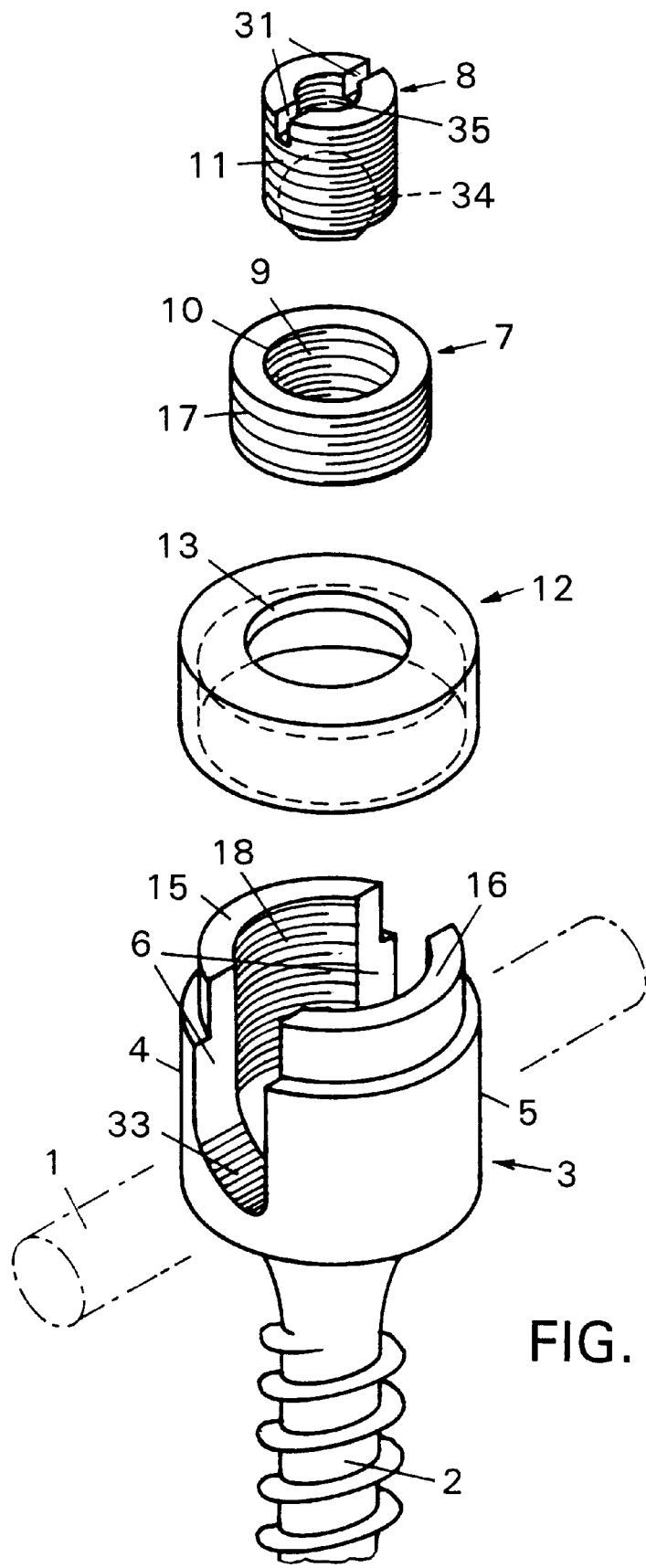
FIG. 1 is an exploded perspective of a spinal implant according to the invention.

Referring to FIG. 1, a spinal implant according to the invention has a head 3 and the anchoring segment 2. The anchoring segment 2 is shown as a pedicle screw which can be screwed into a vertebra. It might alternatively be a spinal hook (not shown). To receive a support rod 1, the head 3 is fitted with a U-shaped slot 6 formed by two legs 4, 5. An internal thread 18 is present in the upper part of the head 3. A cylindrical closure 7 has a thread 17 engaging the inner thread 18, so that it can be screwed into the U-shaped slot 6. Closure 7 has a central borehole 10 fitted with an inner thread 9.

A fastener 8 is provided. It has an outer thread 11 matching the inner thread 9 and thus can be screwed into the borehole 10. For easier handling, the fastener 8 is fitted with a slot 31 at the top. A movable spheroidal contact element 34 is installed at the bottom of fastener 8.

Figure 1A:
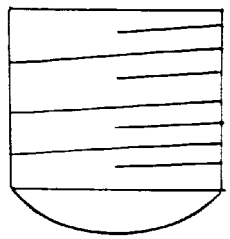
FIG. 1A is a view in side elevation of a fastener for use in the invention having a domed contact surface.
Figure 1B:
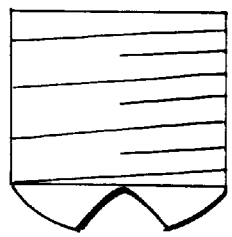
FIG. 1B is a view in side elevation of a fastener for use in the invention having a conically concave contact surface.
Figure 1C:
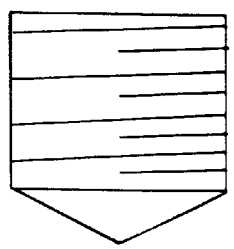
FIG. 1C is a view in side elevation of a fastener for use in the invention having a pointed contact.

As shown in FIG. 1, the element 34 has the shape of a ball with a flattened face. Alternatively, the element 34 may be a complete sphere or it may have a concave contact surface to fit the curvature of the support rod 1. In place of the contact element 34, fastener 8 may have a convex or domed surface as shown in FIG. 1A. Alternatively, a conical countersink may be used as shown in FIG. 1B. As a further alternative, the end of the fastener may be pointed as shown in FIG. 1C.

The implant may further include a safety bush 12. It is a cup-like element having a collar 13 at the top. The safety bush 12 is slipped over the narrowed upper ends 15, 16 of the legs 4, 5 of the head 3. In another embodiment, not shown, the safety bush 12 may be made integral with the closure part 7.

Figure 1D:
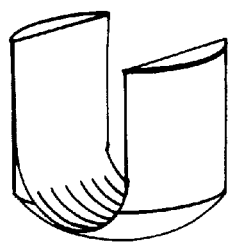
FIG. 1D is a schematic perspective view of the bottom of a screw head according to the invention with transverse serrations.

The bottom of slot 6 may be roughened or provided with longitudinal serrations 33 as shown in FIG. 1 or with transverse serrations as shown schematically in FIG. 1D.

Appropriately, the core diameter of the inner thread 18 in the head 3, and correspondingly the outer thread 17 of the closure part 7, is in the range of 8 to 12 mm, preferably 9.5 to 10.5 mm. The diameter of the fastener 8 is in the range of 7–9 mm, preferably 7.5 to 8.5 mm. The width of the U-shaped slot 6 in the head 3, and the diameter of the support rod 6 in the head, are in the range of 5–7 mm, preferably 5.5 to 6.5 mm.

In the course of surgery, the anchoring element 2 is screwed into the vertebra to be corrected or stabilized and a support rod 1 is inserted into the slot 6 of the head. Thereupon, the closure 7 is rotated axially from above in the slot 6 until the upper edge is flush with the two legs 15, 16. The remaining distance between the support rod 1 and the lower edge of the closure part 7 is between 1 and 4 mm, preferably between 1.5 and 2.5 mm. The fastener 8 already may have been slightly screwed into the closure part 7. In the light of clinical experience so far, the screws in the various vertebra are always mounted in such manner that enough space is available to screw in the closure part 7. This is also the case when hooks are used.

Unless the safety bush 12 is rigidly joined to the closure part 7, it should be mounted before tightening the fastener 8. The bush prevents the legs 4, 5 from spreading.

The fastener 8 (which may have a temporary extension piece, not shown, for ease of handling) is then screwed into the closure 7 until the contact element 34 rests on the support rod 1. The fastener is then tightened. As a result, the support rod 1 is clamped in the U-slot 6. The contact element 34 is of such a shape that the clamping force increases proportionally when the support rod 1 is loaded in its longitudinal direction. Following clamping, if an extension piece has been used, it is removed from the fastener 8.

The fore going procedure may be used with the other implants described in connection with FIGS. 2–7 below.

The above described spinal implant of the invention offers many advantages. The fastener 8 clamping the support rod 1 is guided in a closed thread and is screwed in only after the support rod 1 has been properly positioned. Contrary to the practice with conventional implants having posterior apertures, the slotted thread 18 in the head 3 is not used for tightening but only to position the closure 7. The fastener 8 may already be slightly screwed into the closure part 7 before the latter is itself screwed in. As a result, the closure part is easily handled. The outside diameter of the fastening devices 7, 8 and the safety bush 12 being no larger than, or smaller than, the outside diameter of the head 3, the implant is not enlarged over what it would be without the securing structure.

In FIGS. 2–5, the closures are affixed to the head by bayonet locks rather than screws. As shown in FIG. 1, the fastener may be screwed into a full inner thread in the closure.

Figure 2:
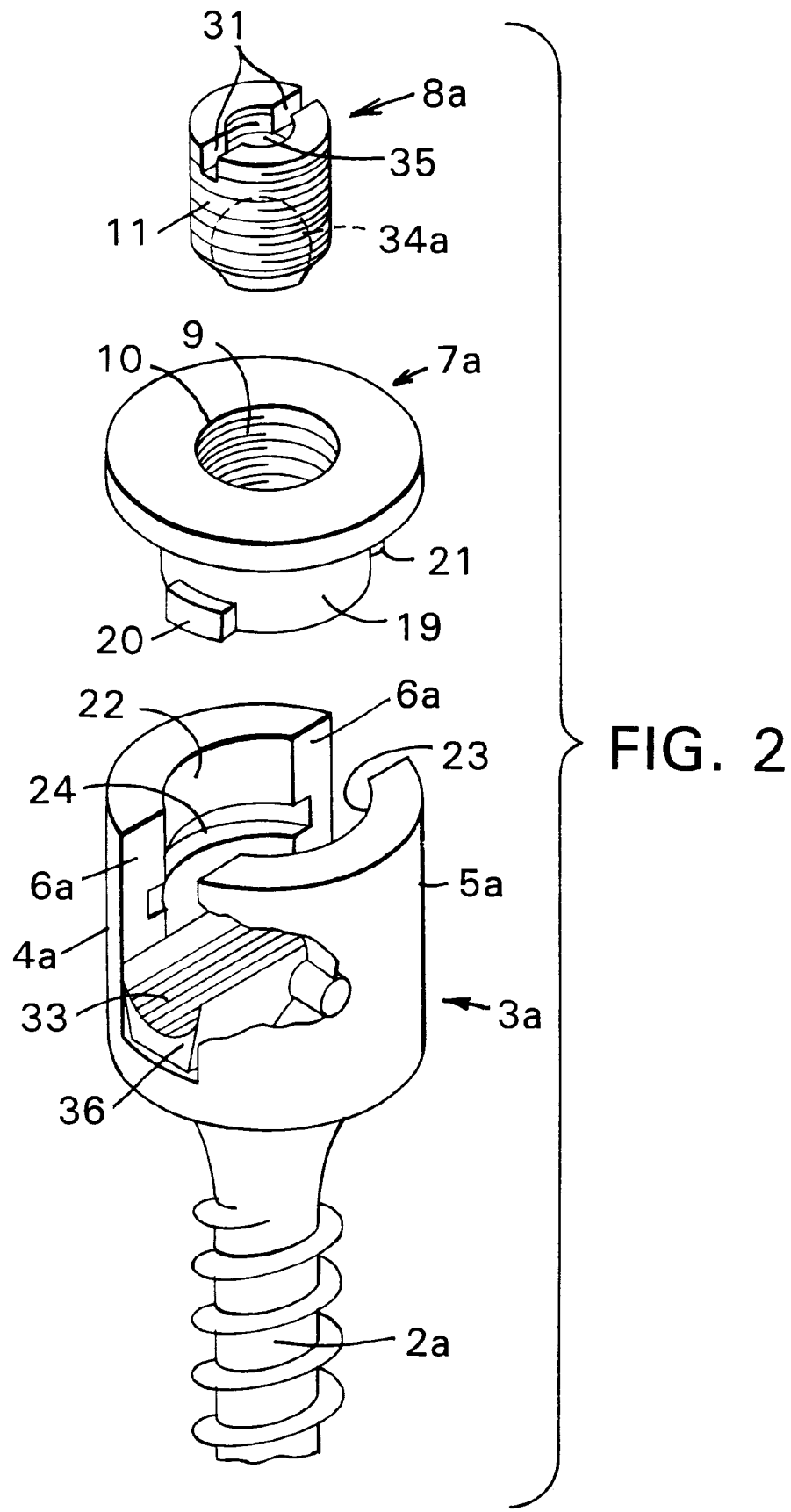
FIGS. 2–5 are exploded perspective views of further embodiments of spinal implants according to the invention.

Referring specifically to FIG. 2, the closure 7a is fitted with two diametrically opposite studs 20, 21 on its surface 19. In the inner walls 22, 23 of the legs 4a, 5a, of the U-shaped slot 6a, of head 3a, are provided two arcuate channels such as 24, for said studs 20, 21. After the closure 7a has been axially inserted, it is rotated in the slot 6a and in the process the studs 20 and 21 are inserted into the channels such as 24.

In the embodiment of FIG. 2, the fastener 8a may also comprise at its bottom a rotatable, spheroidal contacting element 34a. The element 34a may be a true sphere, not shown, or may have a flattened surface or a cylindrical concave surface to provide a better fit to the surface geometry of the support rod. Such elements are described in published European patent application 0 572 790 A1.

The base of the U-shaped slot 6a comprises a floor extending in the longitudinal direction of said base in which is seated a movable element 36 with longitudinal serrations 33, the displacement of the element 36 being determined by the geometry of the U-shaped slot.

Figure 3:
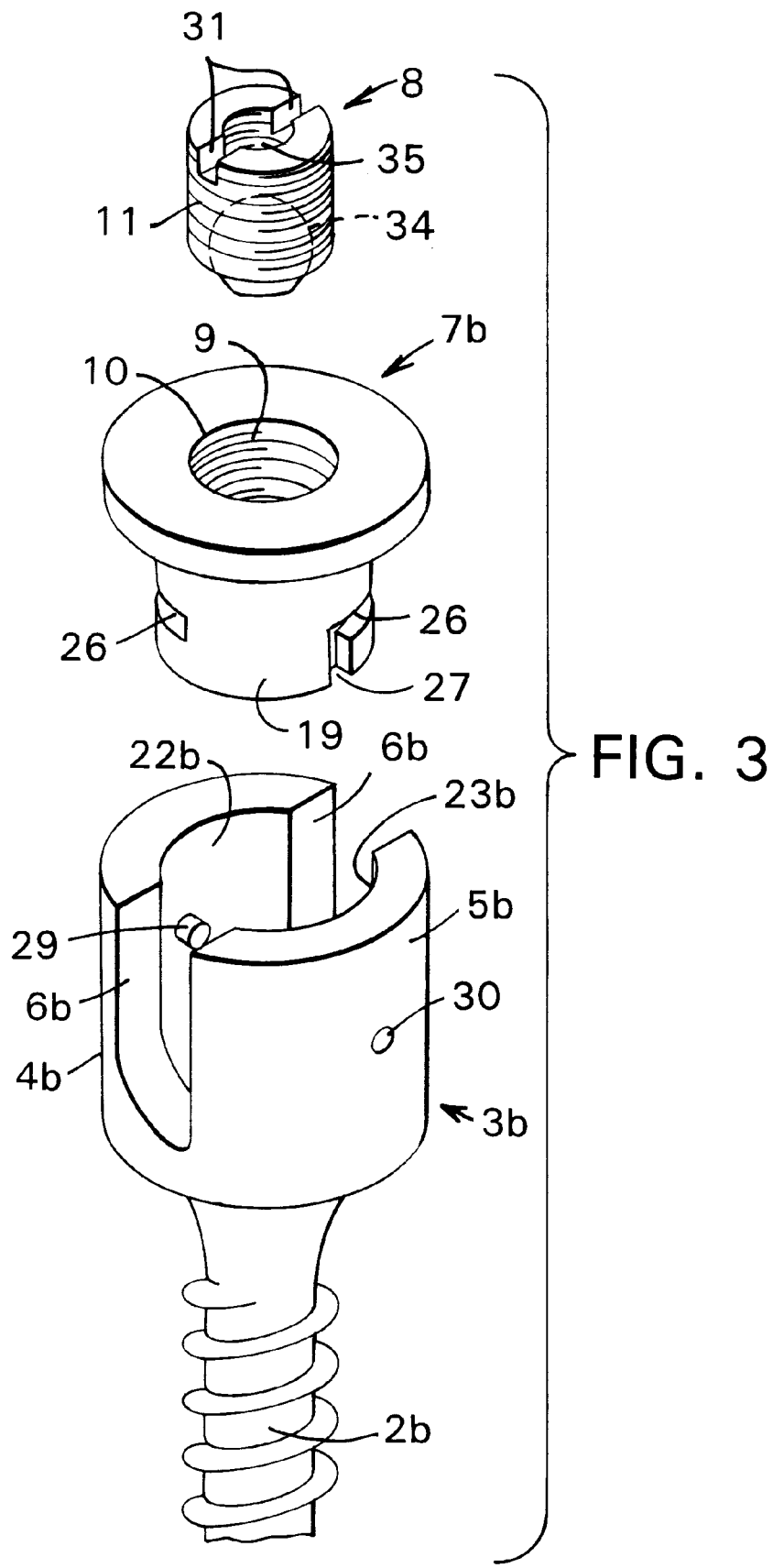

In FIG. 3 the closure component 7b is fitted with a circular transverse channel 26 and two longitudinal channels 27 on opposite sides of its surface 19. The longitudinal channels 27 coincide in position and direction with studs 29, 30 located on the inner sides 22b, 23b of the legs 4b, 5b. After the closure part 7b has been axially inserted into the U-slot 6b, the studs 29b, 30b can be inserted by rotation into the circular transverse channel 26. Preferably the circular transverse channel 26 runs less than the full circumference of the closure element 7b.

A safety bush is not mandatory in the embodiments shown in FIGS. 2 and 3 because the two legs 4a, 5a, 4b, 5b do not tend to spread when the fasteners 8a, 8b are tightened because the closures are bayonet-type.

Figure 4:
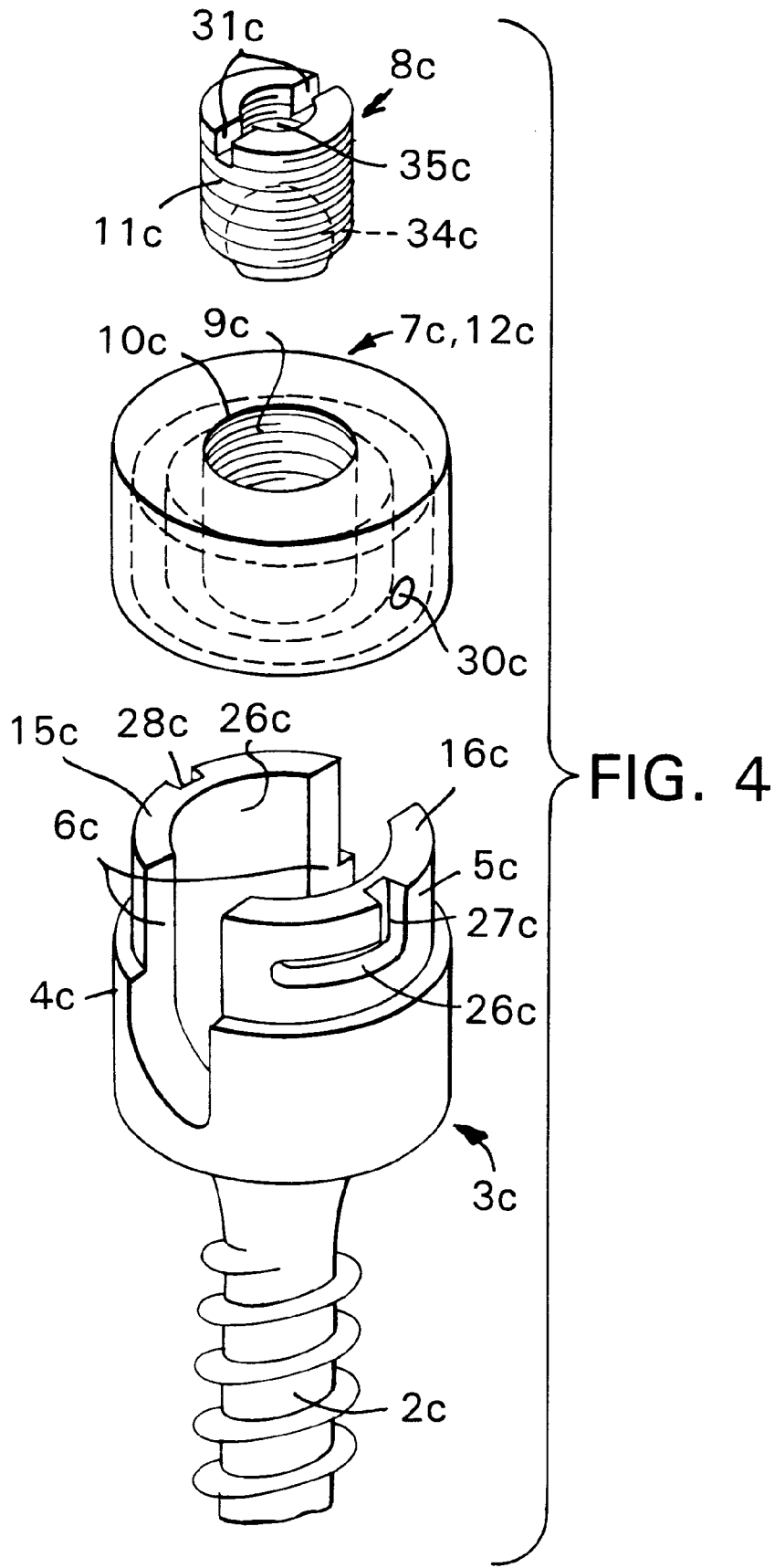

FIG. 4 shows an embodiment mode in which the closure part 7c and the safety bush 12c are integral. The closure part 7c is locked in the affixing head 3c in a manner similar to that shown in FIGS. 2 and 3. The transverse channel 26c with longitudinal arms 27c, 28c appears in this embodiment on the outer surface of the upwardly narrowed leg ends 15c, 16c of the head 3c instead of on the inside of the legs 4c, 5c. The longitudinal arms 27c, 28c coincide in position and direction with studs such as 30c inside the safety bush 12c. After the closure part 7c has been axially inserted into the U-slot 6c, the studs such as 30c can be rotated into the circular transverse channel 26c.

Figure 5:
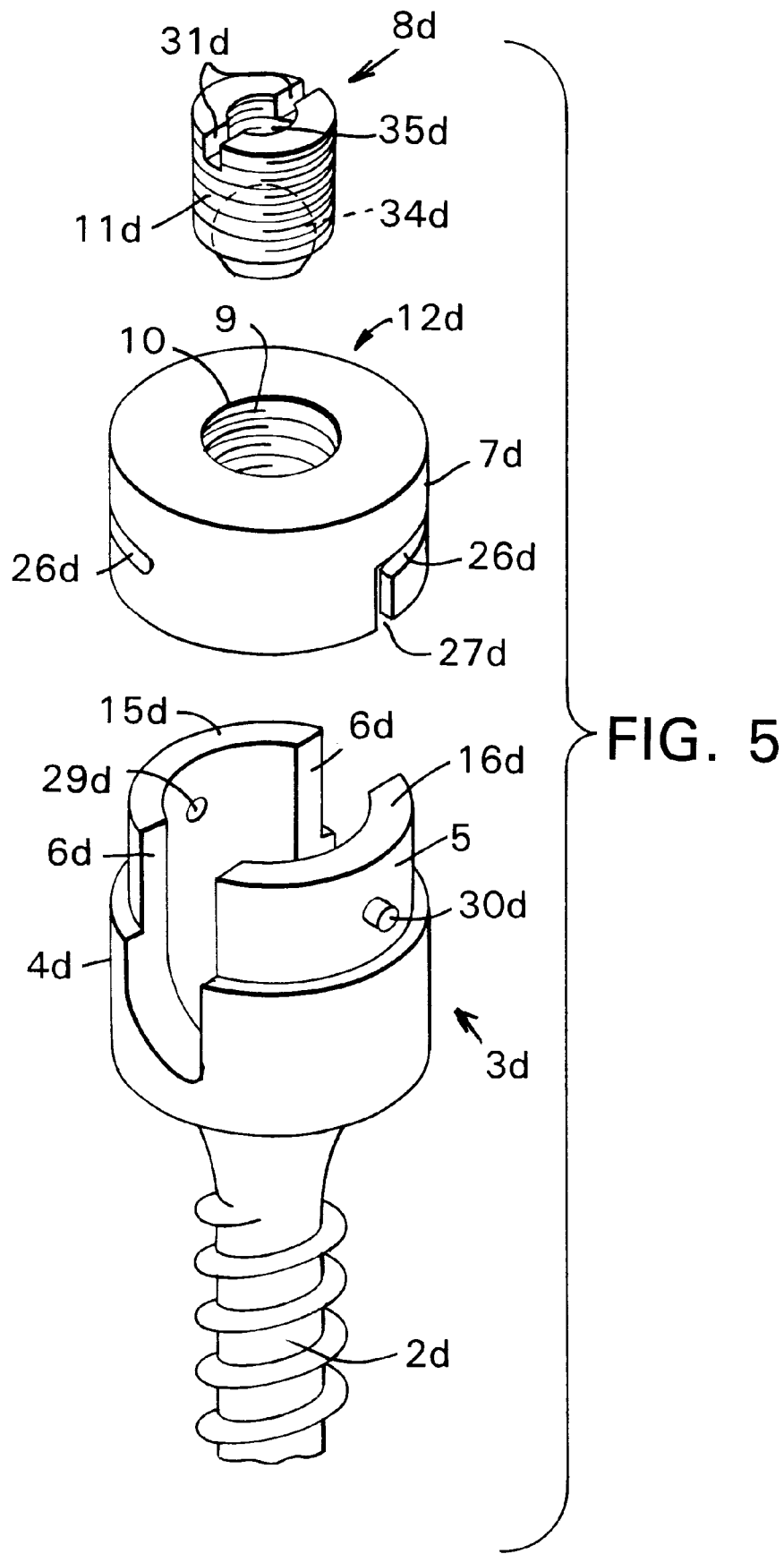

FIG. 5 shows an embodiment reciprocal to that of FIG. 4 wherein the circular transverse channel 26d together with its longitudinal channels such as 27d are present in the safety bush 12d and the studs 29d, 30d are present on the outer surface of the upwardly narrowed leg ends 15d, 16d of the head.

Figure 6:
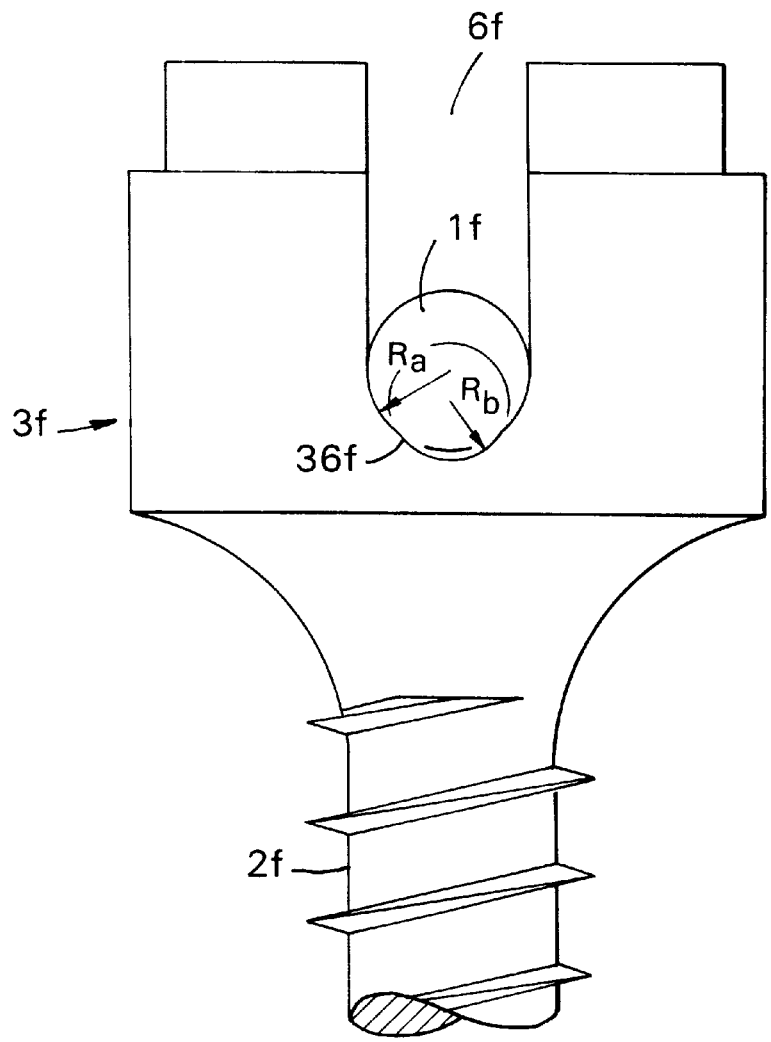
FIG. 6 is a longitudinal section of the head of a spinal implant according to the invention.

FIG. 6 shows an embodiment in which the base 36f of the U-shaped slot 6f of the head 3f comprises a double radius $R_a$, $R_b$ to accommodate support rods of different diameters.

Figure 7:
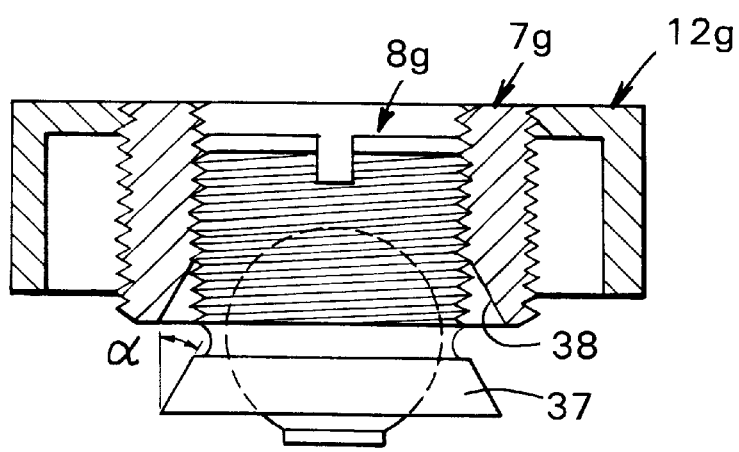
FIG. 7 is a longitudinal section of the closure and fastener of a spinal implant according to the invention.

Lastly, FIG. 7 shows a preferred embodiment of the invention in which the fastener 8g is fitted with a flange 37 at its end facing a support rod (not shown). At its side away from the support rod, the flange 37 subtends an angle of between 0 and 90°, preferably between 45 and 60°. The closure element 7g has a corresponding bevel 38.

The flange 37 and the bevel 38 serve to strongly and mutually brace the closure part 7g prior to implantation in such manner that the closure part 7g and the fastener 8g act as a unit up to a given torque and separate only after this torque has been exceeded. Separation takes place when the closure part 7g or the stabilizing bush 12g are stopped when being screwed in and only the fastener 8g is able to penetrate further until coming to rest against the support rod which it then starts clamping.

What is claimed is:

1. A spinal implant kit for attachment of the implant to the spine and for clamping a support rod, said implant kit comprising (a) an anchoring segment for attachment to the spine, (b) a head attached to said anchoring segment, said head comprising two legs defining a transverse slot for receiving a support rod, (c) a cylindrical closure element having an aperture and locking means adapted for engagement with said legs, and (d) a fastener adapted to be inserted through said aperture and to clamp within said slot at least the largest diameter cylindrical support rod capable of passing through said slot, and (e) a safety bush element adapted to surround at least a portion of said legs;

said head further comprising a stop located at a position preventing said safety bush from clamping any cylindrical support rod capable of passing through said slot.

2. The implant kit claimed in claim 1 wherein the aperture is centrally located in said closure element and has an internal thread.

3. The implant kit claimed in claim 2, wherein the fastener has an external thread matching the internal thread of the aperture.

4. The implant kit claimed in claim 1 wherein the outside diameter of the closure element is not greater than the outer diameter of the head.

5. The implant kit claimed in claim 1 wherein each of said legs has an end remote from said anchoring segment, the ends of the legs are narrowed, and the bush has an inner diameter such that it can be slipped over the ends of the legs and an outer diameter no greater than the outer diameter of the head.

6. The implant kit claimed in claim 5, wherein the safety bush comprises a collar having an opening large enough to allow passage of the fastener.

7. The implant kit claimed in claim 5, wherein the safety bush comprises a flange having a aperture large enough to accommodate the fastener.

8. The implant kit claimed in claim 1 wherein the safety bush and closure element are formed integrally.

9. The implant kit claimed in claim 1 wherein the bush and closure element are connected to one another.

10. The implant kit claimed in claim 1 wherein the closure element has an outer thread and the slot has a matching inner thread.

11. The implant kit claimed in claim 1 wherein the closure element comprises a stud and a leg of the slot has a matching arcuate transverse channel to receive said stud thus to form a bayonet type closure element.

12. The implant kit claimed in claim 1 wherein the closure element comprises a transverse channel and two longitudinal channels connecting to said transverse channel and the inner surfaces of the legs have studs for insertion into said channels to lock said closure element in said slot.

13. The implant kit claimed in claim 11 wherein the transverse channel extends over less than the full circumference of the head.

14. The implant kit claimed in claim 12 wherein the transverse channel extends over less than the full circumference of the closure element.

15. The implant kit claimed in claim 1 wherein the fastener is a set screw having a central aperture.

16. The implant kit claimed in claim 15 wherein the aperture of the fastener is threaded.

17. The implant kit claimed in claim 15 wherein the set screw comprises a convex surface.

18. The implant kit claimed in claim 17 wherein the convex surface has a countersink.

19. The implant kit claimed in claim 18 wherein the countersink is conical.

20. The implant kit claimed in claim 15, wherein the set screw tapers to a point.

21. The implant kit claimed in claim 1 wherein the base of the slot is serrated.

22. The implant kit claimed in claim 1 wherein the base of the slot has a first, relatively small radius in a central region at the bottom of the slot and a second, relatively larger radius on either side of said central region.

23. The implant kit claimed in claim 1 wherein the diameter of the closure element is in the range of 8 to 12 mm.

24. The implant kit claimed in claim 23 wherein the diameter of the closure element is in the range 9.5 to 10.5 mm.

25. The implant kit claimed in claim 1 wherein the diameter of the fastener is in the range of 7 to 9 mm.

26. The implant kit claimed in claim 25 wherein the fastener diameter is in the range 7.5 to 8.5 mm.

27. The implant kit claimed in claim 1 wherein the width of the slot is in the range of 5 to 7 mm.

28. The implant kit claimed in claim 27 wherein the width of the slot is in the range 5.5 to 6.5 mm.

29. The implant kit claimed in claim 1 wherein the base of the slot comprises a recess for receiving a movable element for contacting a support rod inserted in said slot.

30. A spinal implant kit for attachment of the implant to the spine and for clamping a support rod, said implant kit comprising (a) an anchoring segment for attachment to the spine, (b) a head attached to said anchoring segment, said head comprising two legs defining a transverse slot for receiving a support rod, (c) a cylindrical closure element having an aperture and locking means adapted for engagement with said legs, (d) a fastener adapted to be inserted through said aperture and to clamp within said slot at least the largest diameter cylindrical support rod capable of passing through said slot, and (e) a safety bush element adapted to surround at least a portion of said legs;

said head further comprising a stop located at a position preventing said safety bush from clamping any cylindrical support rod capable of passing through said slot, wherein the fastener comprises a rotatable, spheroidal contacting element.

31. The implant kit claimed in claim 30 wherein the fastener comprises a spherical contact element having a portion cut away to provide a surface for contacting said support rod.

32. A spinal implant kit for attachment of the implant to the spine and for clamping a support rod, said implant kit comprising (a) an anchoring segment for attachment to the spine, (b) a head attached to said anchoring segment, said head comprising two legs defining a transverse slot for receiving a support rod, (c) a cylindrical closure element having an aperture and locking means adapted for engagement with said legs, and (d) a fastener adapted to be inserted through said aperture and to clamp within said slot at least the largest diameter cylindrical support rod capable of passing through said slot, and (e) a safety bush element adapted to surround at least a portion of said legs;

said head further comprising a stop located at a position preventing said safety bush from clamping any cylindrical support rod capable of passing through said slot, wherein the fastener comprises a flange at the end of said fastener closest to the anchoring segment.

33. The implant kit claimed in claim 32, wherein the flange has a chamfered surface on the side away from the anchoring element comprising an angle between 0 and 90°.

34. The implant kit claimed in claim 33 wherein the angle is between 45° and 60°.

35. The implant kit claimed in claim 33 wherein the closure element comprises a countersink matching the chamfered surface of the flange.

36. A spinal implant kit for attachment of the implant to the spine and for clamping a support rod, said implant kit comprising
   (a) an anchoring screw for attachment to the spine, and
   (b) a cylindrical head attached at one end to and coaxial with said anchoring screw, said head comprising
      (1) two legs defining a transverse slot for receiving a support rod, and
      (2) an internally threaded recess between said legs,
   (c) a cylindrical closure element having a central, axial aperture and having external threads adapted for engagement with said internally threaded recess,
   (d) a fastener adapted for insertion through said aperture to clamp a support rod within said slot,
   (e) a safety bush adapted for surrounding at least a portion of the legs, said safety bush having an outer diameter no greater than the outer diameter of the head, and
   said head further comprising a stop adapted to prevent said safety bush from contacting the largest diameter cylindrical support rod which can be clamped in said slot by said fastener.

37. A spinal implant kit for attachment of the implant to the spine and for clamping a support rod, said implant kit comprising
   (a) an anchoring segment for attachment to the spine,
   (b) a head attached to said anchoring segment, said head comprising two legs defining a transverse slot for receiving said support rod,
   (c) a cylindrical closure element having an aperture and locking means adapted for engagement with said legs, and
   (d) a fastener comprising an externally threaded member adapted to be inserted in said aperture and a rotatable contacting element.

38. The implant kit claimed in claim 37 wherein said fastener is adapted to clamp within said slot at least the largest diameter cylindrical support rod capable of passing through said slot.

39. The implant kit claimed in claim 37 wherein a major portion of said contacting element is spherical.

40. The implant kit claimed in claim 37 wherein a portion of said contacting element is cut away to provide a surface for contacting said support rod.

41. The implant kit claimed in claim 37 wherein the base of said slot is serrated.

42. The implant kit claimed in claim 37 wherein the base of the slot has a first, relatively small radius in a central region at the bottom of the slot and a second, relatively larger radius on either side of said central region.

43. The implant kit claimed in claim 37 wherein said fastener is adapted to clamp within said slot at least the largest diameter cylindrical support rod capable of passing through said slot, a major portion of said contacting element is spherical and a portion of said contacting element is cut away to provide a surface for contacting said support rod.

44. The implant kit claimed in claim 43 wherein the base of said slot is serrated.

45. The implant kit claimed in claim 43 wherein the base of said slot has a plurality of radii.

46. A spinal implant kit for attachment of the implant to the spine and for clamping a support rod, said implant kit comprising
   (a) an anchoring segment for attachment to the spine,
   (b) a head attached to said anchoring segment, said head comprising two legs defining a transverse slot for receiving a support rod,
   (c) a cylindrical closure element having an aperture and locking means adapted for engagement with said legs, and
   (d) a fastener adapted to be inserted in said aperture and to clamp within said slot at least the largest diameter cylindrical rod capable of passing through said slot, and wherein the fastener comprises a flange at the end of said fastener closest to the anchoring segment.

47. The implant kit claimed in claim 46 wherein the flange has a chamfered surface on the side away from the anchoring element comprising an angle between 0 and 90°.

48. The implant kit claimed in claim 47 wherein the angle is between 45° and 60°.

49. The implant kit claimed in claim 47 wherein the closure element comprises a countersink matching the chamfered surface on said flange.

50. The implant kit claimed in claim 48 wherein the closure element comprises a countersink matching the chamfered surface on said flange.

\* \* \* \* \*